(12) United States Patent
Cannon et al.

(10) Patent No.: US 11,685,674 B2
(45) Date of Patent: Jun. 27, 2023

(54) WATER TREATMENT

(71) Applicant: VEOLIA WATER SOLUTIONS & TECHNOLOGIES SUPPORT, SAS, Saint Maurice (FR)

(72) Inventors: Andrew Cannon, High Wycombe (GB); William Jeal, High Wycombe (GB)

(73) Assignee: VEOLIA WATER SOLUTIONS & TECHNOLOGIES SUPPORT, SAS, Saint Maurice (FR)

( * ) Notice: Subject to any disclaimer, the term of this patent is extended or adjusted under 35 U.S.C. 154(b) by 0 days.

(21) Appl. No.: 16/484,932

(22) PCT Filed: Feb. 9, 2018

(86) PCT No.: PCT/GB2018/050372
§ 371 (c)(1),
(2) Date: Aug. 9, 2019

(87) PCT Pub. No.: WO2018/146488
PCT Pub. Date: Aug. 16, 2018

(65) Prior Publication Data
US 2019/0382295 A1 Dec. 19, 2019

(30) Foreign Application Priority Data
Feb. 10, 2017 (GB) ...................................... 1702272

(51) Int. Cl.
*C02F 3/00* (2023.01)
*C02F 3/08* (2023.01)
(Continued)

(52) U.S. Cl.
CPC .............. *C02F 3/006* (2013.01); *C02F 3/085* (2013.01); *C02F 3/20* (2013.01); *C12M 1/12* (2013.01);
(Continued)

(58) Field of Classification Search
CPC .. C02F 3/006; C02F 3/085; C02F 3/20; C02F 2209/14; C02F 2209/22; C02F 2209/44; C12M 1/12; C12M 25/20
(Continued)

(56) References Cited

U.S. PATENT DOCUMENTS 5,458,779 A  10/1995 Odegaard
5,525,230 A   6/1996 Wrigley et al.
(Continued)

FOREIGN PATENT DOCUMENTS

CN  101364083 A   2/2009
CN  105084534 A  11/2015
(Continued)

OTHER PUBLICATIONS

International Search Report dated Apr. 24, 2018.
(Continued)

*Primary Examiner* — Claire A Norris
(74) *Attorney, Agent, or Firm* — Caesar Rivise, PC

(57) ABSTRACT

A water treatment apparatus (1), the apparatus (1) comprises a fluid inlet (2), a first MBBR (4) and a second MBBR (5) and a fluid outlet (3), and a controller (C1), wherein the first MBBR (4) and second MBBR (5) are connected in series such that water to be treated flows from the inlet (2) through the first MBBR (4) to the second MBBR (5) and thence to the outlet (3) and wherein the controller or control means (C1) is operable to change the flow direction such that water to be treated flows from the inlet (2) to the second MBBR (5) then to the first MBBR (4) and thence to the outlet (3).

16 Claims, 3 Drawing Sheets

(51) Int. Cl.
*C02F 3/20* (2023.01)
*C12M 1/12* (2006.01)

(52) U.S. Cl.
CPC ......... *C12M 25/20* (2013.01); *C02F 2209/14* (2013.01); *C02F 2209/22* (2013.01); *C02F 2209/44* (2013.01)

(58) Field of Classification Search
USPC ......................................................... 210/614
See application file for complete search history.

(56) References Cited

U.S. PATENT DOCUMENTS

| | | | | | |
|---|---|---|---|---|---|
| 6,630,067 | B2* | 10/2003 | Shieh | ...................... | C02F 3/301 |
| | | | | | 119/227 |
| 7,862,722 | B2* | 1/2011 | Moon | ..................... | C02F 3/006 |
| | | | | | 210/143 |
| 2010/0018919 | A1 | 1/2010 | Lee et al. | | |
| 2011/0284461 | A1 | 11/2011 | DiMassimo et al. | | |
| 2012/0152814 | A1* | 6/2012 | Lean | ....................... | C02F 3/085 |
| | | | | | 210/202 |
| 2013/0264280 | A1 | 10/2013 | Zhao et al. | | |
| 2014/0238931 | A1* | 8/2014 | DiMassimo | .......... | C02F 3/1263 |
| | | | | | 210/604 |

FOREIGN PATENT DOCUMENTS

| | | | |
|---|---|---|---|
| CN | 105641996 | A | 6/2016 |
| CN | 105645589 | A | 6/2016 |
| CN | 205917068 | U * | 2/2017 |
| EP | 0598752 | B1 | 5/1997 |

OTHER PUBLICATIONS

English language abstract of CN101364083A.
English language abstract of CN105641996A.
English language abstract of CN105645589A.
English language abstract of CN105084534A.

* cited by examiner

WATER TREATMENT

CROSS-REFERENCE TO RELATED APPLICATIONS

This application is a U.S. National Phase Application of PCT/GB2018/050372, filed Feb. 9, 2018, which claims priority to GB Patent Application No. 1702272.4, filed Feb. 10, 2017, the contents of which applications are incorporated herein by reference in their entireties for all purposes.

BACKGROUND OF THE INVENTION

This invention relates generally to water treatment and more particularly to moving bed biofilm reactors (MBBRs) used in the treatment of waste water.

It is known to use biological methods for the treatment of waste water. These methods are deployed in various apparatus such as rotating biological contactors, biorotors, trickling filters and MBBRs.

MBBRs were invented in the late 1980s and have been commercialised worldwide. An example of a MBBR is described in U.S. Pat. No. 5,458,779.

Typically, a MBBR comprises a tank or reactor in which a plurality of carriers is located together with the waste water to be treated. The surface of each carrier provides a site for the formation and growth of biofilm. Usually the carriers have a density which approximates that of water, for example carriers may be fabricated from high density polyethylene which has a density of about 0.95 g cm$^{-3}$. The carriers are mixed or agitated within the tank by mechanical stirrers or by air which is forced into the tank. This causes the carriers (and hence the attached biofilm) to be continuously mixed with the waste water, and thus to contact the constituents of the waste water. Contact of the waste water with the biofilm leads to the removal of the pollutants from the waste water. The tank is provided with a sieve or screen on the downstream portion to prevent egress of the carriers whilst allowing the cleaned water to exit the tank. Accordingly, MBBRs operate to continuously clean influent waste water. As the microbial population increases on a carrier, clumps of microorganisms may break away from the carriers. Any such solids are held in suspension by the turbulence and are discharged from the MBBR with the treated water. The solids will be settled out in a subsequent process step.

MBBRs may be deployed as a secondary treatment stage to reduce the organic matter content (under US Environmental Protection Agency standards secondary treatment is expected to produce effluent with a monthly average of less than 30 mg/l biochemical oxygen demand (BOD) and less than 30 mg/l suspended solids). Also, MBBRs may be deployed as at least a part of a tertiary treatment stages wherein preferably up to 100% BOD and suspended solids is removed.

In most countries it is a requirement that water has a certain quality before it is released. In England and Wales, discharge consents (i.e. consent to allow discharge) for discharge from a sewage treatment plant are awarded by the Environment Agency under a procedure described in Schedule 10 of the Water Resources Act 1991. Similar procedures are in place to control industrial discharges. Other countries have similar bodies which provide authorisation for discharges.

In many countries the discharge consents (or equivalents) are awarded, at least in part, on the ability to lower the amount of ammonia and phosphorous within the treated water. In MBBRs it is known to deploy nitrifying bacteria on the carriers which are able to oxidise the ammonia within the waste water to be treated and reduce the ammonia level to within consent discharge limits. However, using an MBBR it may be difficult to deal with a peak demand incident wherein a temporary unexpected peak load of ammonia is within the waste water to be treated. It is possible to provide MBBRs in parallel to provide redundancy but this is wasteful during 'normal' operating conditions and may not provide a system which is capable of attending to 'peak' or unexpected loads.

Accordingly, there is a need to provide effective and efficient water treatment apparatus which is able to attend to unexpected and/or high peak demand.

A first aspect of the invention provides water treatment apparatus, the apparatus comprising a fluid inlet, a first MBBR and a second MBBR and a fluid outlet, and a controller or control means, wherein the first MBBR and second MBBR are connected in series such that water to be treated flows from the inlet through the first MBBR to the second MBBR and thence to the outlet and wherein the controller or control means is operable to change the flow direction such that water to be treated flows from the inlet to the second MBBR then to the first MBBR and thence to the outlet.

A further aspect of the invention provides a method of treating waste water, the method comprising the steps of:
 a) flowing waste water through an inlet to a first MBBR and thence to a second MBBR and thence to an outlet
 b) after a period of time changing the flow direction such that waste water flows from the inlet to the second MBBR and thence to the first MBBR and thence to the outlet.

Advantageously, the reversal of flow maintains an even development of biofilm within each MBBR. Biofilm within a MBBR will develop according to the pollutant load applied and will decay if the pollutant load is insufficient to support growth. By reversing the flow it is possible to maintain the biofilm profile in each of the serial MBBRs. In fact, by operating the MBBRs in series the 'lag' MBBR may be provided with a pollutant load which is sufficient to maintain the biofilm or at least reduce the rate of decay of biofilm. Thus, upon flow reversal the 'lag' MBBR (which then becomes the 'lead' MBBR) will have sufficient biofilm population to commence treatment of the influent waste water. Moreover, the reversal of flow allows two MBBRs to operate efficiently.

The flow reversal may occur periodically. The periodicity of flow reversal may be daily, for example every 12 hours, 24 hours, 36 hours or 48 hours.

The apparatus may comprise sensors, for example water quality sensors, to determine one or more physical and/or chemical properties of the water. In an embodiment the apparatus comprises a sensor to determine one or more physical and/or chemical properties of the water to be treated. Additionally or alternatively the apparatus may comprise a sensor to determine one or more physical and/or chemical properties of the water which has been treated. The apparatus may comprise sensors to determine one or more physical and/or chemical properties of the water within one or other or both of the MBBRs. The controller may be operable to reverse the flow through the first and second MBBRs depending on parameters determined by a sensor, or by parameters determined by a plurality of sensors.

The apparatus may comprise an ammonia sensor to determine the level of ammonia upstream, within and/or downstream thereof. The flow through the MBBRs may be reversed dependent upon ammonia concentration, load or flux.

Advantageously, if a peak load of ammonia is detected or monitored, the flow direction through the apparatus can be controlled to make effective use of the biofilm within each MBBR.

The method may comprise reversing the flow through the apparatus in dependence on an elapsed process time, and/or as a result of a characteristic of the water upstream, within or downstream of the MBBRs and/or the apparatus.

A protocol may be deployed whereby flow reversal may occur as a function of elapsed treatment time unless a characteristic of the water upstream, within and/or downstream of one or other or both of the MBBRs passes a respective threshold, whereby the flow is reversed.

The apparatus may comprise air blowers to aerate the fluid within each MBBR. Each MBBR may be provided with a sensor to detect the dissolved oxygen concentration. The air blowers may be controllable in dependence upon one or more operating parameters of the apparatus and/or characteristics of the water upstream, within or downstream of the respective MBBR, for example the dissolved oxygen concentration within one or both of the MBBRs.

The apparatus may comprise a human-machine interface, whereby operating parameters of the apparatus may be selected. The method may comprise selecting operating parameters, for example using a HMI.

DETAILED DESCRIPTION OF THE PREFERRED EMBODIMENTS

In order that the invention may be more fully understood, it will now be described, by way of example only, and with reference to the accompanying drawings, in which.

Figure 1:
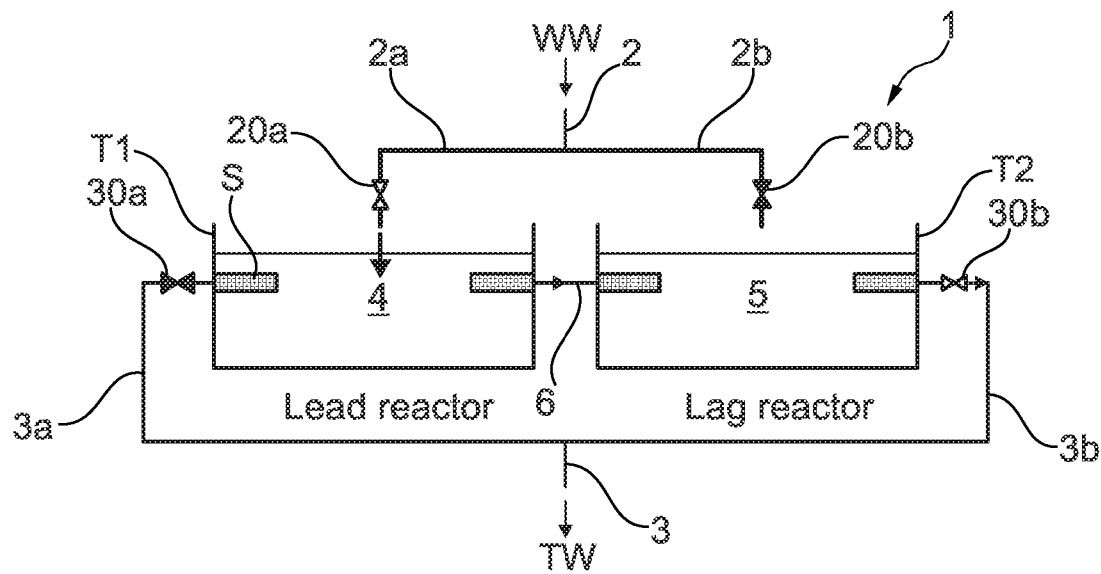
FIG. 1 shows a water treatment apparatus according to the invention.

Referring to FIG. 1 there is provided a water treatment apparatus 1 having an inlet 2 for receipt of waste water WW to be treated and an outlet 3 for delivery of treated water TW. The apparatus 1 further comprises a first MBBR 4 having a first tank T1 and a second MBBR 5 having a second tank T2, the two MBBRs 4, 5 being connected in series via a conduit 6. Each Tank T1, T2 is provided with screens S to cover the various points of egress from the tanks T1, T2 to ensure the retention of the carriers (not shown) within the tanks T1, T2.

The carriers usually occupy up to 65% of the volume of each tank T1, T2 although this may be varied depending on operating requirements.

The inlet 2 is branched to provide two separate conduits, a first inlet conduit 2a extending to the first MBBR 4 and a second inlet conduit 2b extending to the second MBBR 5. Each conduit 2a, 2b is provided with respective valves 20a, 20b to control flow of waste water WW into the respective tanks T1, T2.

Each tank T1, T2 is provided with respective outlet conduits 3a, 3b which converge at the outlet 3. The outlet conduits 3a, 3b are provide with respective valves 30a, 30b to control fluid flow therethrough.

In operation, waste water WW flows into the inlet 2 and, because the valve 20b is closed to occlude the second inlet conduit 2b, flows along the first inlet conduit 2a and into the tank T1 of the first MBBR 4 whereupon the waste water is treated by contact with carriers (not shown) carrying biofilm. In the usual fashion, the contents of the tank T1 are agitated mechanically by a rotor or impeller (not shown) or are aerated by air blown or forced in the tank T1 by air blowers (not shown).

As shown in FIG. 1, the valve 30a is closed which prevents fluid flow from the first tank T1 along the first outlet conduit 30a and thereby ensures that fluid flow from the first tank T1 is along conduit 6 and into the second tank T2 of the second MBBR 5. The fluid is then contacted by carriers (not shown) carrying biofilm within the second tank T2. Again, the contents of the second tank T2 are agitated mechanically by a rotor or impeller (not shown) or are aerated and agitated by air forced or blown into the second tank T2 by air blowers (not shown) in the usual manner.

Treated water TW is able to exit the second tank T2 along the second outlet conduit 3b via the open valve 30b and to the outlet 3.

As will be appreciated, in the configuration shown the first MBBR 4 may be termed the 'lead' reactor and the second MBBR may be termed the 'lag' reactor.

Figure 2:
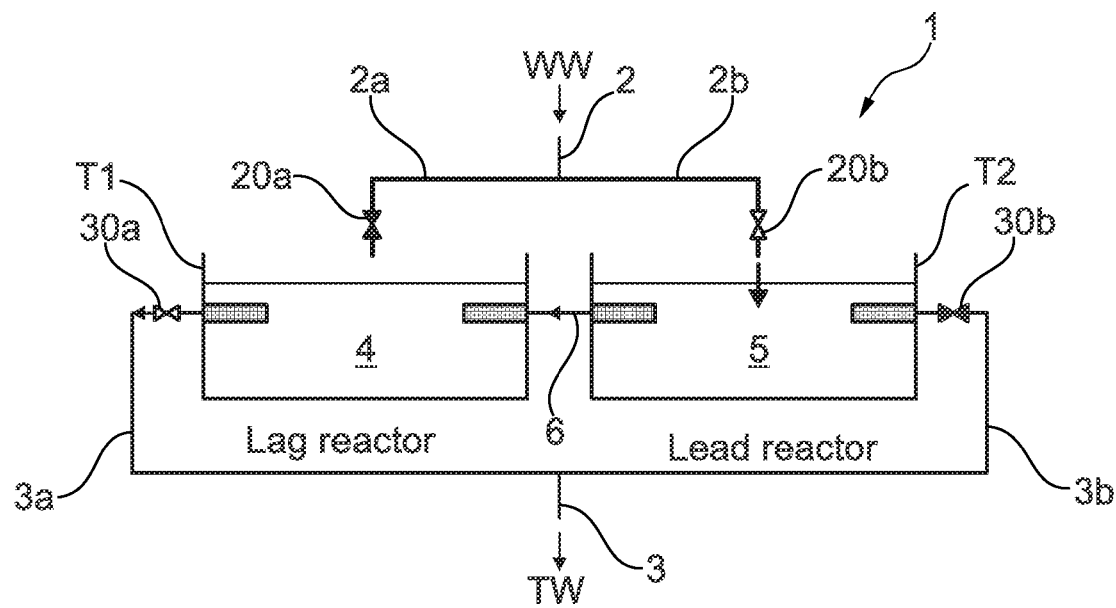
FIG. 2 shows the water treatment apparatus of FIG. 1 in a second operating configuration.

Referring now to FIG. 2, the apparatus 1 is shown in a second configuration, whereby valve 20a is closed, valve 20b is open, valve 30b is closed and valve 30a is open. As will be appreciated, by changing the status of the valves, the direction of flow along the conduit 6 has been altered and the second MBBR 5 is now the lead reactor and the first MBBR 4 is now the 'lag' reactor. Accordingly, waste water WW flows from the inlet 2 along inlet conduit 2b into the tank T2 of the second MBBR 5 along the conduit 6 and into the tank T1 of the first MBBR 4 and then along the outlet conduit 3a to deliver treated water TW to the outlet 3.

Figure 3:
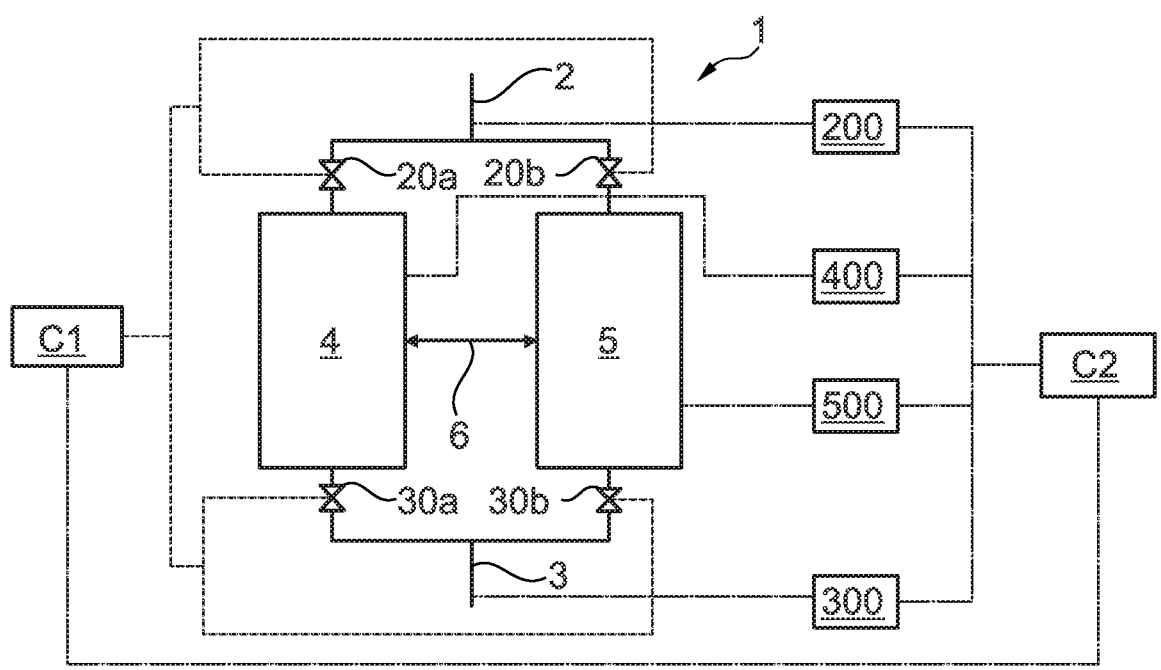
FIG. 3 is a schematic representation of the control system for the apparatus of FIG. 1.

Referring now to FIG. 3, there is a shown a schematic representation of the water treatment apparatus 1. As can be seen, each of the valves 20a, 20b, 30a, 30b are operably connected (indicated by dashed lines) to a controller C1. The controller C1, which may comprise a computer processor, is operable to alter the operating status of the valves from closed to open and vice versa to change the flow directions through the apparatus 1 and thereby to alternate flows from the configuration shown in FIG. 1 to that shown in FIG. 2 and back again. In one embodiment the controller C1 may be arranged to change the flow direction periodically, for example after a set time period such as 24 hours. Conveniently, if the flow direction is altered every twenty four hours this may be completed at a period of low demand on the apparatus 1, for example during the night. Alternatively, the time period may be any other time period.

Additionally or alternatively, the apparatus may be provided with one or more sensors to monitor the characteristics of the water within the apparatus 1. For example, the apparatus may be provided with a sensor to monitor or determine the nature of the influent waste water WW (indicated as waste water sensor 200) and/or to monitor or determine the nature of the effluent treated water TW (indicated as treated water sensor 300). Each of the influent waste water sensor 200 and/or the effluent treated water sensor 300 may monitor or determine one or more physical or chemical characteristics of the fluid flowing in the respective inlet 2 or outlet 3. If present the waste water sensor 200 and/or the effluent treated water sensor 300 may be connected to a second controller C2 (which may be the controller C1 or may be operably connected to the controller C1) and the output of the waste water sensor 200 and/or the effluent treated water sensor 300 may be used to determine whether or not to prompt the controller C1 to change the operating configuration of the apparatus 1 (i.e. from the configuration shown in FIG. 1 to that shown FIG. 2 or vice versa), depending on the monitored characteristics of the influent waste water WW and/or effluent treated water TW. One or both of the first MBBR 4 and the second MBBR 5 may be provided with sensors 400, 500 to monitor one or more operating characteristics within the respective reactor. The operating characteristics may be physical or chemical characteristics (for example dissolved oxygen concentration, nitrogen concentration and so on). The or each sensor 400, 500 may be operably connected to the second controller C2 and the outputs of the or each sensor 400, 500 may be used to determine if the controller C1 should be prompted to change the operating configuration of the apparatus 1 (i.e. from the configuration shown in FIG. 1 to that shown FIG. 2 or vice versa).

Accordingly, the water treatment apparatus 1 of the invention may be used to treat water according to a control philosophy which states that the flow direction within the apparatus will reverse periodically, for example, every 24 hours. A more sophisticated control philosophy might state that the flow direction within the apparatus will reverse periodically, for example, every 24 hours unless one or more of the sensors 200, 300, 400, 500 detects that the respective fluid is outside of operating parameters. In those circumstances the controller C1 may be deployed to alter the flow direction through the apparatus 1 as soon as, or after detection of the characteristic outside of operating parameters.

The invention will now be described by reference to the following illustrative example

EXAMPLE 1

In a particular embodiment of the invention, each reactor 4, 5 is partially filled with small plastic elements or carriers, each of which may be approximately 25 mm in diameter (suitable carriers are known from the prior art). Nitrifying bacteria attach themselves to the surfaces of the plastic elements. Each reactor 4, 5 is filled with wastewater WW. Air, providing oxygen for the ammonia oxidation reaction, is blown in at the base of the reactor 4, 5. The plastic elements are of approximately neutral buoyancy and circulate freely within the reactor 4, 5 due to the mixing effect of the aeration. Sieves over each influent and effluent port retain the plastic media within the reactor 4, 5. As the microbial population increases, clumps of microorganisms break away from the media. These solids are held in suspension by the turbulence within the reactor 4, 5 and are discharged with the treated effluent.

On a regular basis the flow path through the two reactors 4, 5 reverses so that the lead reactor (e.g. the first MBBR 4) becomes the lag reactor and vice versa. This ensures that the nitrifying bacteria in the lag reactor remain active despite the low residual loads.

Air is supplied by two blowers, normally (i.e. other than during the initial media conditioning period) arranged as duty and standby. Air may be introduced into each MBBR reactor via, for example, four fine bubble diffuser grids. The air supply to each grid can be isolated by actuated valves. Supplying air to only the downstream side of a reactor creates a swirling mixing pattern with a current along the surface moving away from the outlet sieves. This prevents media accumulating at the downstream end of a reactor. The actuated valves allow the mixing pattern to be reversed when the flow path reverses. An air flow modulating valve is provided for each reactor. Air lances are installed beneath each sieve to provide supplementary mixing. A sieve is only aerated when flow through it is directed outwards.

A dissolved oxygen sensor (400, 500) is preferably installed in each MBBR 4, 5 respectively. An ammonia sensor 300 is preferably installed downstream of the MBBR.

The aeration rate within an MBBR (4 or 5) is controlled to minimise power consumption while providing sufficient oxygen and mixing energy to meet the process objectives. The ammonia sensor measures the effluent ammonia concentration on a regular, nominally 15 minute, cycle. The ammonia measurement is used to adjust the aeration operating mode of the plant.

Three operating modes are available:
1. Intermittent aeration of both reactors at a fixed low air flow
2. Continuous aeration of both reactors; the lead reactor under Dissolved Oxygen (DO) control to a low set point and the lag reactor at a fixed low air flow.
3. Continuous aeration of both reactors; the lead reactor under DO control to a high set point and the lag reactor at a fixed low air flow.

In addition, two options, selectable via the Human-Machine Interface (HMI), are available for the intermittent aeration mode.
1. Combined intermittent aeration
2. Independent intermittent aeration Combined intermittent aeration allows the blower to operate at higher, more energy efficient flow rates, avoids the head loss associated with the modulating valves and maximises the mixing energy at the start of a period of aeration. Independent intermittent aeration provides greater operation flexibility in that different aeration cycles can be used in each reactor.

If the ammonia concentration is less than the "Maximum ammonia concentration for intermittent aeration" and the Combined intermittent aeration option has been selected, the MBBRs 4, 5 are aerated intermittently by stopping and starting the blower. When the "Combined intermittent aeration cycle time" timer times out the blower operates at the "Combined intermittent aeration blower speed" for the "Combined minimum intermittent aeration blower on period" and until the dissolved oxygen (DO) concentration in the lead reactor reaches the "Minimum DO in the lead reactor during intermittent aeration". The air modulating valves are driven to the "Combined intermittent aeration lead reactor modulating valve position" and the "Combined intermittent aeration lag reactor modulating valve position"

If the ammonia concentration is less than the Maximum ammonia concentration for intermittent aeration and the Independent intermittent aeration option has been selected, the reactors are aerated intermittently by opening and closing the appropriate (see below) aeration grid isolation valves. The modulating valves are driven to the "Independent intermittent aeration lead reactor modulating valve position" and the "Independent intermittent aeration lag reactor modulating valve position". When the "Independent intermittent aeration lead reactor cycle time" timer times out the lead reactor air grid isolating valves open for the "Minimum independent intermittent aeration lead reactor on period" and until the DO concentration in the lead reactor reaches the Minimum DO in the lead reactor during intermittent aeration. When the "Independent intermittent aeration lag reactor cycle time" timer times out the appropriate (see below) lag reactor air grid isolating valves open for the duration of the "Minimum independent intermittent aeration lag reactor on period". The blower speed varies in response to the pressure in the manifold to maintain an operator adjustable "Blower main pressure" set point. If all air grid isolating valves close the blower stops. The blower restarts when an isolating valve opens. The current values of the cycle timers are displayed on the HMI.

If the ammonia concentration is greater than the Maximum ammonia concentration for intermittent aeration", the air flow to the lead reactor modulates to maintain the dissolved oxygen concentration in the lead reactor at the "Lead reactor low dissolved oxygen set point". The lead reactor modulating valve operates between the "Lead reactor continuous aeration minimum modulating valve position" and the "lead reactor continuous aeration maximum modulating valve position". The modulating valve for the lag reactor is driven to the "Lag reactor continuous aeration modulating valve position". The blower speed is controlled to maintain the pressure in the air main at the Blower main pressure set point.

If the ammonia concentration is greater than the "Maximum ammonia concentration for continuous low dissolved oxygen aeration", the air flow to the lead reactor modulates to maintain the dissolved oxygen concentration in the lead reactor at the "Lead reactor high dissolved oxygen set point". The lead reactor modulating valve operates between the Lead reactor continuous aeration minimum modulating valve position and the Lead reactor continuous aeration maximum modulating valve position. The modulating valve for the lag reactor is driven to the Lag reactor continuous aeration modulating valve position. The blower speed is controlled to maintain the pressure in the air main at the Blower main pressure set point.

In the event that the DO analyser in the lead reactor develops a fault, or if it is selected out of service while the plant is aeration modes 2 or 3 (continuous aeration), the lead reactor modulating valve is driven to the Lead reactor continuous aeration maximum modulating valve position. If either condition occurs while the plant is in aeration mode 1, combined intermittent option, then the duration of each period of aeration is extended until the next cycle begins. In effect aeration is supplied continuously at a fixed rate. Similarly, if the independent aeration option has been selected aeration is supplied continuously to the lead reactor. In essence the philosophy is that if the DO is not known it is assumed to be low, representing the worst case.

The aeration control philosophy is summarised in the table below:

lating valve at a given position to drop. The actual air flows corresponding to the valve limit positions should be checked periodically (e.g. annually) using the or a installed flow meter and the set points adjusted if required.

The automatic control system can be operated without the ammonia sensor. This option can be selected via the HMI. When the ammonia sensor is selected out of service or is faulty or its signal is out of range, both reactors are aerated continuously with the aeration to the lead reactor under DO control to maintain the Lead reactor high dissolved oxygen set point.

Each MBBR 4, 5 may be equipped with four separate air diffuser grids and two pairs of sieves S at opposite sides over the inlet and outlet ports. The longitudinal axis of each aeration grid is oriented at right angles to the sieves. The air supply to each grid can be isolated individually by actuated valves. The division of air between the grids which are receiving air can be adjusted by manual valves. By tapering the aeration away from the outlet sieves a spiral roll mixing pattern is created which helps to draw the media away from the outlet sieves.

The air grids in use during intermittent aeration can be specified via the HMI by selecting each grid, 1-4, in the lead reactor and the lag reactor as either on or off. Grid 1 is the grid beneath the outlet sieves. At the beginning of a period of aeration during intermittent aeration the air can be directed to only the grid beneath the outlet sieves for a period, the "Grid 1 advance start time", to initiate mixing. If the Grid 1 advance start timer is greater than zero and the Combined intermittent aeration option is selected the actuated valves supplying the selected grids other than the grid beneath the outlet sieves close when the blower stops. When the blower starts, the actuated valves supplying the selected grids other than Grid 1 open after the Grid 1 advance start timer delay. Similarly if the Independent aeration option is selected when an aeration period starts the actuated valves supplying the selected grids other than Grid 1 open after the Grid 1 advance start timer delay.

The air grids in use during continuous aeration can be specified via the HMI by selecting each grid, 1-4, in the lead reactor (e.g. the first MBBR 4) and the lag reactor (e.g. the second MBBR 5) as either on or off. Different grid configurations can be used for intermittent and continuous aeration. This allows a configuration providing high mixing energy to be used for intermittent aeration and a configuration which maximises oxygen transfer to be used for continuous aeration.

TABLE 1

Aeration Control Philosophy

| Measured ammonia | Lead reactor | Lag reactor |
|---|---|---|
| $NH_4 > 0.9$ mg/l | Continuous aeration to maintain high DO<br>Blower controls air main pressure<br>Air control valve controls DO | Continuous aeration<br>Air control valve set to fixed position |
| $0.6 < NH_4 < 0.9$ mg/l | Continuous aeration to maintain low DO<br>Blower controls air main pressure<br>Air control valve controls DO | Continuous aeration<br>Air control valve set to fixed position |
| $NH_4 < 0.5$ mg/l | Intermittent aeration at fixed air flow | Intermittent aeration at fixed air flow |

Over time the headloss across the membrane diffusers may increase causing the air flow passing through a modu- The grids are physically identified as A, B, C, D in each reactor. The allocation of each grid as 1, 2,3, 4 changes depending on which MBBR is the lead and which is the lag. When the reactor sequence is reversed the numeric designation of the grids also reverses. The designation "Grid 1" always refers to the grid beneath the out-flowing sieves.

In other words, if the first MBBR 4 is the lead reactor and the second MBBR 5 is the lag reactor, then:
Lead Reactor Grid 1 is MBBR 4 Air Grid A
Lead Reactor Grid 2 is MBBR 4 Air Grid B
Lead Reactor Grid 3 is MBBR 4 Air Grid C
Lead Reactor Grid 4 is MBBR 4 Air Grid D
Lead Reactor Aeration Control Valve is MBBR 4 valve
Lead Reactor Outlet Sieve Aeration Isolation Valve is MBBR 4 valve
Lag Reactor Grid 1 is MBBR 5 Air Grid D
Lag Reactor Grid 2 is MBBR 5 Air Grid C
Lag Reactor Grid 3 is MBBR 5 Air Grid B
Lag Reactor Grid 4 is MBBR 5 Air Grid A
Lag Reactor Aeration Control Valve is MBBR 5
Lag Reactor Outlet Sieve Aeration Isolation Valve is MBBR 5

Alternatively, if the second MBBR 5 is the lead reactor and the first MBBR 4 is the lag reactor, then:
Lead Reactor Grid 1 is MBBR 5 Air Grid A
Lead Reactor Grid 2 is MBBR 5 Air Grid B
Lead Reactor Grid 3 is MBBR 5 Air Grid C
Lead Reactor Grid 4 is MBBR 5 Air Grid D
Lead Reactor Aeration Control Valve is MBBR 5
Lead Reactor Outlet Sieve Aeration Isolation Valve is MBBR 5
Lag Reactor Grid 1 is MBBR 4 Air Grid D
Lag Reactor Grid 2 is MBBR 4 Air Grid C
Lag Reactor Grid 3 is MBBR 4 Air Grid B
Lag Reactor Grid 4 is MBBR 4 Air Grid A
Lag Reactor Aeration Control Valve is MBBR 4
Lag Reactor Outlet Sieve Aeration Isolation Valve is MBBR 4

As stated above, the direction of flow through the two MBBRs 4, 5 reverses on a regular basis, such that the lead reactor becomes the lag reactor and vice versa. This ensures that the bacteria in the lag reactor have an adequate supply of ammonia to remain active. Immediately after the flow has reversed the wastewater in the former lead reactor forms the final effluent and, as such, its ammonia concentration must be below the appropriate consent standard when the flow reverses. Before the flow reversal procedure is initiated the system evaluates the likely ammonia concentration in the lead reactor. During the procedure, steps are taken to minimise the ammonia concentration in the lead reactor before it becomes the lag reactor.

To estimate the load the apparatus 1 is treating and so evaluate the ammonia concentration in the lead reactor, a rolling average of the blower operating time over the preceding hour, the "Blower operating fraction", is calculated. The HMI allows up to three times of day to be specified when flow reversal will be initiated if appropriate. When the time of day reaches a "Flow reversal start time" the flow direction change procedure starts, providing the Blower operating fraction is less than the "Blower operating fraction to inhibit flow reversal". If the blower operating fraction is above this limit the flow reversal is deferred until the blower operating fraction drops below the limit providing the deferred time period does not exceed the "Maximum period for which flow reversal can be deferred". If the Maximum period for which flow reversal can be deferred is exceeded the attempt to initiate the flow reversal procedure is abandoned until the next specified time and an alarm is raised. If no Flow reversal start times are specified the flow reversal is inhibited and the current flow direction will be maintained permanently.

The level in the lead reactor will be slightly higher than the level in the lag reactor. To reduce the hydraulic surge when the lead reactor becomes the lag reactor and discharges directly the inlet valves change over slightly before the outlet valves. This period, during which there is no flow through the lead reactor, also provides an opportunity to reduce the ammonia in the lead reactor before it starts to discharge final effluent.

When the flow reversal procedure is initiated the blower speed is set to the "Blower speed during flow reversal" and the modulating valves are driven to the "Flow reversal modulating valve position". Both reactors are aerated continuously. When the "Period of continuous aeration prior to flow reversal" timer times out the procedure continues with the steps listed below 1. Flag "Flow reversing"
2. Start a "Maximum flow reversal time" timer
3. Open incoming lead reactor inlet valve and confirm opened
4. Close outgoing lead reactor inlet valve and confirm closed
5. Start timer equal to "Open outlet delay on reversing flow" and wait to expire
6. Open all of the air grid actuated isolating valves which are not already open and confirm open. At the end of Step 6 all eight air grids should be in use to avoid a transient state with no air valves open as the aeration taper reverses.
7. Open outgoing lead reactor outlet valve and confirm open
8. Close incoming lead reactor outlet valve and confirm closed
9. Reset the air grid and sieve numeric allocation in accordance with the incoming hydraulic sequence and revert to normal operation of the grids and sieves
10. Change the DO signal used for blower control to the incoming lead reactor
11. Change indication of lead/lag reactor
12. Remove flag and reset Maximum flow reversal time timer. If the timer expires before the flag is reset an alarm is raised: "Flow reversing sequence failed"

If the correct valve positions are not confirmed an alarm is raised. If the flow reversal sequence fails or all the air valves do not reach the appropriate positions there is a possibility that the media will accumulate around the sieves causing the water level to rise. This is addressed below.

A high level switch may be installed in each MBBR 4, 5. If either switch operates the actuated valve supplying air to the respective outlet sieves opens for 30 seconds and then returns to normal control. An alarm is raised. If the high level switch is still activated after scouring the sieves for 30 seconds the MBBR inlet wastewater valve closes and an alarm is raised. The flow reversal timer is frozen so that a flow reversal procedure cannot be initiated. Aeration continues as normal.

If both inlet wastewater valves are closed the flow bypasses the apparatus 1.

Periodically it will be necessary to replace the air diffuser membranes. This will require each MBBR 4, 5 in turn to be drained after transferring the media to the remaining reactor.

There are the following selections available at the HMI:
Reactor 1 bypassed
Reactor 2 bypassed If a reactor is bypassed the programmable logic controller (PLC) opens the inlet and outlet water valves on the remaining reactor and when these are confirmed open closes the inlet and outlet water valves on the reactor to be bypassed. The DO set point for the remaining reactor is set to the Lead reactor high dissolved oxygen set point. The blower is controlled directly by the DO and the reactor is aerated continuously. The blower is prevented from operating at a speed below "The minimum blower speed to maintain mixing in a single reactor". The air isolating valves on the bypassed tank are closed. The air modulating valve on the active reactor is driven fully open. The air grid actuated isolating valves on the active reactor which are not already open are opened. This allows the air flows to all four grids to be adjusted using the manual flow balancing valves in order to produce a suitable mixing pattern.

A media transfer pipe equipped with an isolating valve (not shown) connects the two tanks T1, T2. Its purpose is to facilitate the transfer of media from one reactor to the other to allow a reactor to be drained for maintenance. During media transfer both reactors are aerated continuously. This can be accomplished by selecting manual control mode 2 or 3 as described below. The oxygen demand in the downstream reactor will increase steadily as the media migrates. To provide more air in the lag reactor than in the lead reactor the Lead reactor continuous aeration maximum modulating valve position is set to a value just greater than the Lead reactor continuous aeration minimum modulating valve position and the Lag reactor continuous aeration modulating valve position is increased until the blower is operating close to its full output. When the media has been transferred the reactor to be drained can be bypassed.

In manual control the plant can be put into one of the three aeration modes described above. The following modes can be selected via the HMI

TABLE 2

Manual Selectable Modes

Mode

1 Intermittent aeration at a fixed air flow
2 Continuous aeration to achieve a low DO concentration in the lead reactor
3 Continuous aeration to achieve a high DO concentration in the lead reactor This facility allows the correct operation of a specific operating mode to be checked irrespective of the prevailing ammonia concentration.

Aeration lances may be provided beneath each sieve to provide supplementary mixing in the vicinity of outlet ports. Each pair of sieves has a separate actuated valve to isolate the air supply. When the reactor sequence is reversed the air supplies to the sieves over the inlet ports are isolated.

The aeration mode for the sieves over the outlet ports in both reactors can be selected from:

1. Off
2. Off—continuous
3. Off—synchronised—intermittent
4. Off—synchronised—continuous
5. Intermittent
6. Continuous In Mode 2 the sieve aeration is off when the reactor is not aerated and operates continuously when the reactor is aerated continuously or intermittently.

In Modes 3 and 4 the sieve aeration is off when the reactor is not aerated and synchronised when the reactor is aerated intermittently in which case the sieves are aerated when the grids are aerated. Intermittent operation of the sieve aeration in Mode 3 and continuous operation of the sieve aeration in Mode 4 only occurs when the reactor is aerated continuously. Intermittent sieve aeration is controlled by "Sieve aeration on" and "Sieve aeration off" timers.

In Mode 5, intermittent sieve aeration is controlled by the same Sieve aeration on and Sieve aeration off timers.

In Mode 6, sieve aeration is continuous.

In all modes, sieve aeration is to both lead and lag reactors' outlet sieve only. It's not possible to set the lead and lag reactors to different sieve aeration modes.

The two variable-speed blowers operate in a duty standby configuration so as to maintain an operator-adjustable set-point pressure in the common blower air main or a DO set point as described above.

The variable speed drive (VSD) ramp rate is set so that acceleration from rest to full speed takes approximately 20 seconds.

There are the following operator adjustments for blower duty rotation:
Blower A auto duty period
Blower B auto duty period
Blower duty operation: auto or manual
Manual blower duty selection: blower A or blower B
In addition the following password protected option is available
Enable duty/assist blower operation in continuous aeration mode The duty assist blower operation facility is solely intended for use during commissioning. When the media is first added to the tanks the plastic is hydrophobic and difficult to "wet". Air bubbles tend to become attached to the media increasing its buoyancy. The media can form a static layer part in and part out of the water. Increasing the aeration rate can help to entrain media from the underside of the layer so that the media is gradually drawn into suspension. Once in suspensions the surface characteristics change and the hydrophobicity decreases.

While in auto blower duty operation, when a new blower takes over duty the PLC initiates a timer. When the timer reaches the 'auto duty period' for that blower then the PLC switches duty to the other blower. The "Blower A duty period" and the "Blower B duty period" are operator adjustable. While in manual blower duty operation, the operator can select the duty blower. Operation of blowers A and B together is only permitted when the MBBR is in manual control and Mode 3 has been selected.

If duty/assist operation is enabled while in Mode 3, then if the duty blower is running at 100% for longer than a pre-set period (the "Assist blower start timer") and there is a demand for more air then the duty blower speed is set to 50%, the assist blower is started at 50% and blower main pressure control continues by adjusting the speed of both blowers together. While in duty/assist mode, if the blowers speed commands have been less than 50% for longer than a pre-set period (the "Assist blower stop timer") then the assist blower is stopped, the duty blower speed is set to 100% and blower main pressure control using only the duty blower is resumed.

The PLC inhibits the blowers unless:
At least one MBBR actuated valve is more opened than a preset minimum open position (the "Minimum modulating valve position to inhibit blower operation").

At least two air grid isolating actuated valves which are downstream of open (as defined above) modulating air valves are open Each blower is fitted with a discharge high pressure switch, a discharge low pressure switch and a 'filter restriction' pressure switch. In the event of either condition the PLC will fail the blower. This is latched until reset at HMI.

If a duty blower fails then the PLC will swap the duty to run the other blower.

The PLC generates air main high and low pressure alarms in relation to "Air main high pressure" and "Air main low pressure" set points. The low pressure alarm is only generated if a blower is operating. There are no consequent control actions.

The setpoints used by the control system and their anticipated values are summarised below. These are adjustable via the HMI.

TABLE 3

Operating Set Points

| | |
|---|---|
| Maximum ammonia concentration for intermittent aeration | 0.5 mg/l |
| Combined intermittent aeration cycle time" | 30 minutes |
| Combined intermittent aeration blower speed" | 45 Hz |
| Combined minimum intermittent aeration blower on period | 15 minutes |
| Minimum DO in the lead reactor during intermittent aeration | 3 mg/l |
| Combined intermittent aeration lead reactor modulating valve position | 90% open |
| Combined intermittent aeration lag reactor modulating valve position | 90% open |
| Independent intermittent aeration lead reactor modulating valve position | TBA$^1$ % open (to pass 6 m$^3$/minute) |
| Independent intermittent aeration lag reactor modulating valve position | TBA$^1$ % open (to pass 6 m$^3$/minute) |
| Independent intermittent aeration lead reactor cycle time | 30 minutes |
| Minimum independent intermittent aeration lead reactor on period | 15 minutes |
| Independent intermittent aeration lag reactor cycle time | 20 minutes |
| Minimum independent intermittent aeration lag reactor on period | 5 minutes |
| Blower main pressure | 570 mbar |
| Lead reactor low dissolved oxygen set point | 4 mg/l |
| Lead reactor continuous aeration minimum modulating valve position | TBA$^1$ % open (to pass 6 m$^3$/minute) |
| Lead reactor continuous aeration maximum modulating valve position | TBA$^1$ % open (to pass 7.5 m$^3$/minute) |
| Lag reactor continuous aeration modulating valve position | TBA$^1$ % open (to pass 6 m$^3$/minute) |
| Maximum ammonia concentration for continuous low dissolved oxygen aeration | 0.9 mg/l |
| Lead reactor high dissolved oxygen set point | 6 mg/l |
| Grid 1 advance start time | 2 minutes |
| Flow reversal start time | 00:00 (midnight) |
| Blower operating fraction to inhibit flow reversal | 50% |
| Maximum period for which flow reversal can be deferred | 3 hours |
| Blower speed during flow reversal | 45 Hz |
| Flow reversal modulating valve position | 90% open |
| Period of continuous aeration prior to flow reversal | 15 minutes |
| Maximum flow reversal time | 20 minutes |
| Open outlet delay on reversing flow | 15 minutes |
| The minimum blower speed to maintain mixing in a single reactor | Equivalent to 6 m$^3$/minute |
| Sieve aeration on | 5 minutes |
| Sieve aeration off | 10 minutes |
| Blower A duty period | 24 hours |
| Blower B duty period | 24 hours |
| Assist blower start timer | 5 minutes |

TABLE 3-continued

Operating Set Points

| | |
|---|---|
| Assist blower stop timer | 5 minutes |
| Air main high pressure | 620 mbar |
| Air main low pressure | 500 mbar |
| Minimum modulating valve position to inhibit blower operation | 40% |

Figure 4A:
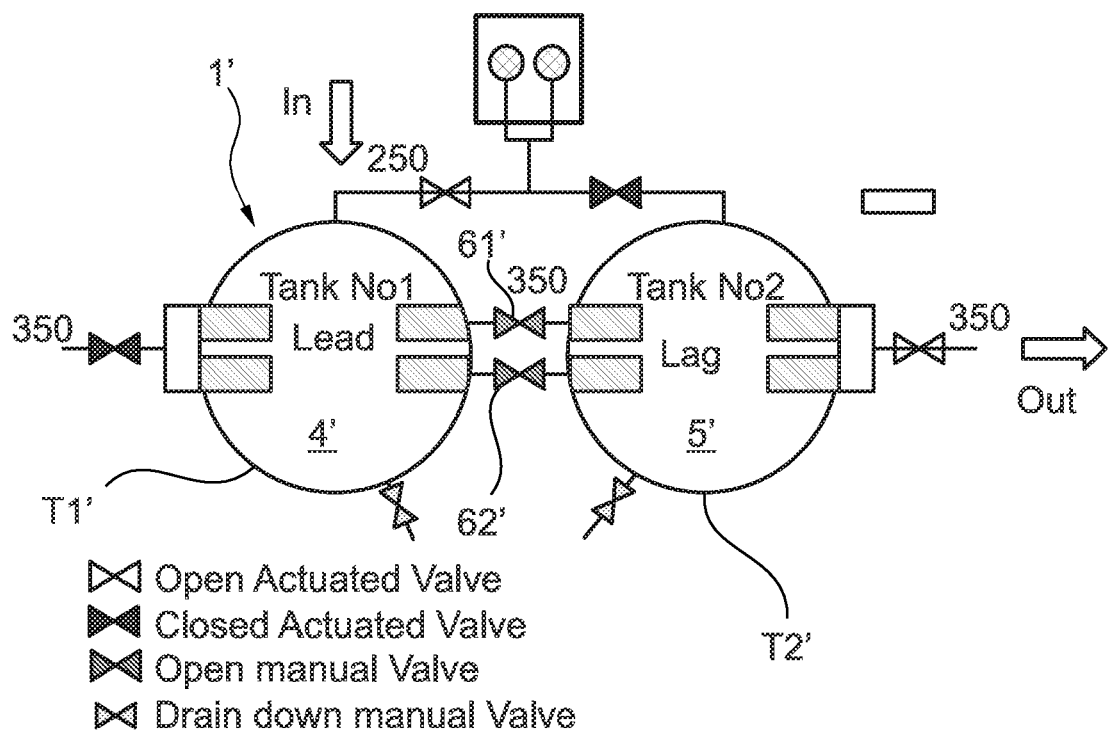
FIGS. 4A and 4B are plan views of a further water treatment apparatus according to the invention in respective first and second configurations.
Figure 4B:
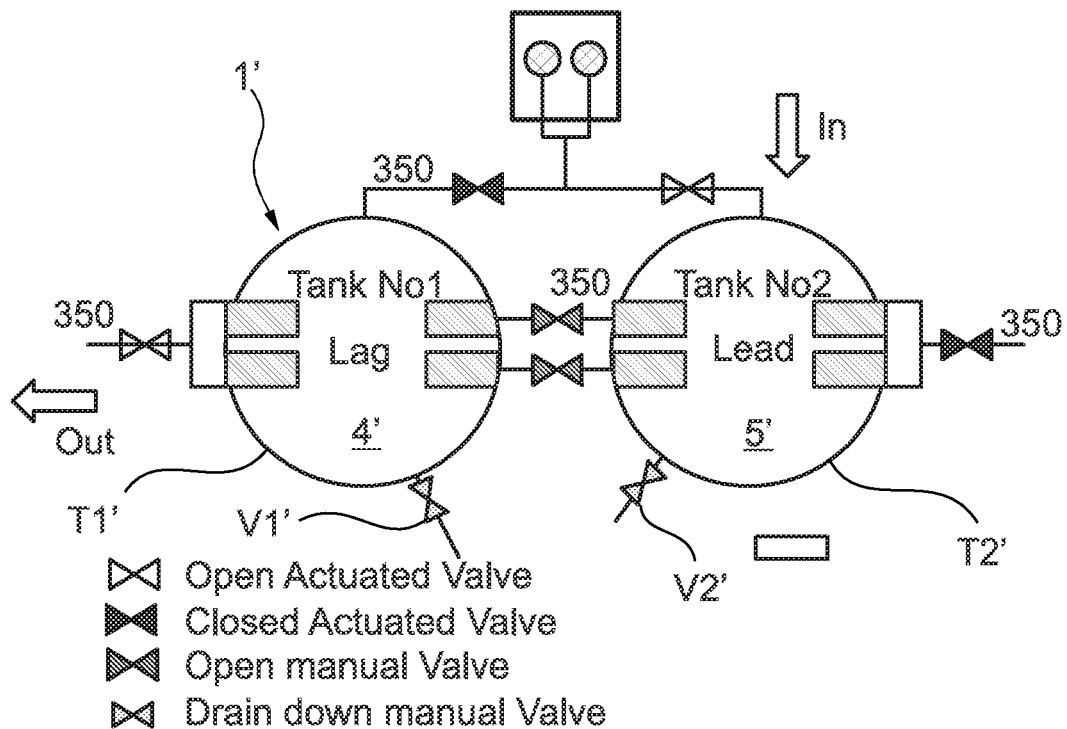

Referring now to FIGS. 4A and 4B, there is shown a further embodiment of the invention comprising apparatus 1' having a first MBBR 4' and a second MBBR 5'. Each of the tanks T1', T2' are provided with drain down valves V1, V2. There are two conduits 61', 62' interconnecting the tanks T1, T2 and each tank T1, T2 is provided with a pair of inlets to receive waste water WW' as appropriate. The operation of the apparatus 1' is as set out above in relation to the first embodiment and/or as set out above in relation to the Example.

It will also be appreciated by those skilled in the art that any number of combinations of the aforementioned features and/or those shown in the appended drawings provide clear advantages over the prior art and are therefore within the scope of the invention described herein.

The invention claimed is:

1. A water treatment apparatus, the apparatus comprising a fluid inlet, a first MBBR and a second MBBR and a fluid outlet, and a controller, each of the first MBBR and the second MBBR having an air blower for aerating the contents of said MBBR configured to generate a dissolved oxygen level of 3 mg/L or greater, wherein the first MBBR and second MBBR are connected in series such that water to be treated flows from the inlet through the first MBBR to the second MBBR and thence to the outlet and wherein the controller is operable to change the flow direction such that water to be treated flows from the inlet to the second MBBR then to the first MBBR and thence to the outlet, wherein the apparatus comprises an ammonia sensor to determine the level of ammonia upstream and/or downstream thereof and wherein the controller is operable to reverse the flow through the first and second MBBRs depending on ammonia concentration, load or flux determined by the ammonia sensor.

2. A water treatment apparatus according to claim 1, comprising further sensors, for example, water quality sensors, to determine one or more physical and/or chemical properties of the water.

3. A water treatment apparatus according to claim 1, comprising a further sensor to determine one or more physical and/or chemical properties of the water to be treated.

4. A water treatment apparatus according to claim 1, comprising a further sensor to determine one or more physical and/or chemical properties of the water which has been treated.

5. A water treatment apparatus according to claim 1, wherein the ammonia sensor and/or further sensor(s) determines one or more physical and/or chemical properties of the water within one or other or both of the MBBRs.

6. A water treatment apparatus according to claim 1, wherein the controller is operable to change the flow through the first and second MBBRs further depending on parameters determined by a further sensor, or by parameters determined by a plurality of further sensors.

7. A water treatment apparatus according to claim 1, wherein the air blower in each MBBR is controllable in dependence upon one or more operating parameters of the apparatus.

8. A water treatment apparatus according to claim 1, wherein the air blower in each MBBR is controllable in dependence upon one or more characteristics of the water upstream, within or downstream of the respective MBBR.

9. A water treatment apparatus according to claim 1, wherein each MBBR is provided with a sensor to detect dissolved oxygen concentration within the MBBR.

10. A water treatment apparatus according to claim 1, wherein each MBBR is provided with a sensor to detect dissolved oxygen concentration and the air blowers are controllable in dependence upon the dissolved oxygen concentration within one or both of the MBBRs.

11. A water treatment apparatus according to claim 1, further comprising a human-machine interface whereby operating parameters of the apparatus may be selected.

12. A method of treating waste water, the method comprising the steps of:
   a. flowing waste water through an inlet to a first MBBR and thence to a second MBBR and thence to an outlet;
   b. aerating the contents of each of the first MBBR and the second MBBR by blowing or forcing air in the MBBR by air blowers to generate a dissolved oxygen level of 3 mg/L or greater;
   c. determining the level of ammonia upstream, within and/or downstream thereof using an ammonia sensor; and
   d. deploying a controller to reverse the flow direction depending on ammonia concentration, load or flux determined by the ammonia sensor, such that waste water flows from the inlet to the second MBBR and thence to the first MBBR and thence to the outlet.

13. A method according to claim 12, further comprising changing the flow periodically.

14. A method according to claim 13, wherein the periodicity of flow changing is daily.

15. A method according to claim 12, further comprising changing the flow through the apparatus in further dependence on an elapsed process time, and/or as a result of a further characteristic of the water upstream, within or downstream of the MBBRs and/or the apparatus.

16. A method according to claim 15, comprising changing the flow through the apparatus in dependence on dissolved oxygen concentration within the MBBRs.

* * * * *